(12) United States Patent
Ghahremani et al.

(10) Patent No.: US 6,206,885 B1
(45) Date of Patent: Mar. 27, 2001

(54) CATHETER GUIDE AND DRILL GUIDE APPARATUS AND METHOD FOR PERPENDICULAR INSERTION INTO A CRANIUM ORIFICE

(76) Inventors: Fathali Ghahremani, 20 Waterside Plz., Apt. 26J, New York, NY (US) 10010; Jamshid Ghajar, 110 E. 71st St., New York, NY (US) 10021

( * ) Notice: Subject to any disclaimer, the term of this patent is extended or adjusted under 35 U.S.C. 154(b) by 0 days.

(21) Appl. No.: 09/290,332

(22) Filed: Apr. 12, 1999

Related U.S. Application Data (60) Provisional application No. 60/081,696, filed on Apr. 14, 1998.

(51) Int. Cl.$^7$ .................................................. A61B 17/58
(52) U.S. Cl. ................................... 606/96; 128/DIG. 26; 604/264
(58) Field of Search ............................... 128/26; 604/264, 604/164, 523; 606/108, 80, 79, 86, 96, 97, 98, 167, 172

(56) References Cited

U.S. PATENT DOCUMENTS

| | | |
|---|---|---|
| 4,821,716 * | 4/1989 | Ghajar et al. ...................... 606/130 |
| 4,931,056 | 6/1990 | Ghajar . |
| 5,520,692 | 5/1996 | Ferrante . |
| 5,611,515 * | 3/1997 | Benderev et al. .................... 128/898 |
| 5,833,693 | 11/1998 | Abrahami . |
| 5,938,686 * | 8/1999 | Benderev et al. ..................... 606/96 |

* cited by examiner

Primary Examiner—Glenn K. Dawson
(74) Attorney, Agent, or Firm—Levisohn, Lerner, Berger & Langsam (57) ABSTRACT

An improved apparatus for drilling an orifice in a human cranium at an angle of substantially 90 degrees to a plane defined by a tangent to the surface of the cranium at the orifice and for guiding ventricular catheter placement. The apparatus has a first tubular guide for directing a drill at the proper angle, the first tubular guide being supported upon the cranium by a plurality of leg members and having a slot or opening which allows for visualization of the drilling point. The invention further includes a second tubular guide for directing a catheter into the ventricular portion of the patient's brain. The second tubular guide, has a slot or opening which allows for pre-loading of the catheter. The second tubular guide inserts within the first tubular guide and receives the catheter and directs it into the ventrical. The slotted design of the first and second tubular guides allow the guides to be removed from the side of the catheter rather than over the end of the catheter.

7 Claims, 8 Drawing Sheets

CATHETER GUIDE AND DRILL GUIDE APPARATUS AND METHOD FOR PERPENDICULAR INSERTION INTO A CRANIUM ORIFICE

RELATED APPLICATIONS

This application claims priority of U.S. Provisional Application Ser. No. 60/081,696, filed Apr. 14, 1998, the contents of which are fully incorporated herein by reference.

FIELD OF THE INVENTION

The invention relates to an improved apparatus and method for penetrating a human cranium at an angle of 90 degrees to the surface. More particularly, the invention relates to an improved guide for a drilling device and an improved guide for ventricular catheter placement to ensure that both the perforation of the cranium and the catheter insertion are oriented at the correct angle of 90 degrees. The drill guide may be used in combination with a drill to ensure the the drill perforates the cranium at the required 90 degree angle. An improved guide for ventricular catheter placement may, subsequent to the removal of the drill, be inserted into the drill guide to facilitate the correct positioning of a catheter device within a ventricular portion of the patient's brain.

BACKGROUND OF THE INVENTION

The four ventricles of the human brain are interconnected cavities that produce and circulate cerebrospinal fluid (CSF). Procedures involving ventriculostomy, i.e., placement of a catheter into the ventricular system of the brain, form a major part of a neurosurgeon's clinical practice. General areas of application of ventricular catheter placement include intracranial pressure monitoring (ICP), draining or shunting of CSF, and the instillation of pharmacological therapeutic agents.

Intracranial pressure monitoring. i.e., the monitoring of ventricular pressure, is critical to the management of patients after severe head trauma, fulminant meningitis, Reyes's syndrome, encephalitis, stroke, cerebral hemorrhage, or subarachnoid hemorrhage producing stupor or coma. However, the ventricles are usually compressed after head trauma and thus they are technically difficult to cannulate for ICP monitoring. Accordingly, subarachnoid pressure monitoring, which is not as true a measure of cerebral pressure as intraventricular pressure monitoring, is generally used.

CSF drainage is essential for patients with congenital or acquired hydrocephalus. This procedure, which can only be performed with an intraventricular catheter, is a life-preserving step, because it can immediately reduce intracranial pressure. The ventricular catheter used to drain cerebrospinal fluid is connected to a peripheral subcutaneous drainage system, i.e., to the peritoneal cavity or systemic circulation via the heart. In hydrocephalus, the ventricles are enlarged and are an easier target for cannulation. However, reports in neurosurgical literature indicate that suboptimal placement in dilated ventricles can subsequently produce catheter obstruction when the ventricles are decompressed and become smaller, thus emphasizing the need for accurate placement.

Catheter placement in cerebral ventricles is widely performed on patients with carcinomatous and fungal meningitis for the administration of well-known antineoplastic and antifungal chemotherapeutic agents, respectively. Invariably, the ventricles in these patients are small or normal sized and difficult to cannulate.

Standard procedures for ventricular catheterization are disclosed in the textbook literature. See, for example, *Neurosurgery*, edited by Robert H. Wilkins and Setti S. Rengachary, Section A, Chapter 13, Techniques of Ventricular Puncture (McGraw Hill 1984).

The most frequently chosen site for ventricular catheterization is the coronal region. In most cases, a catheter is inserted in the anterior horn of the lateral ventricle through an orifice or burr hole drilled just anterior to the coronal suture in the midpupillary line of the cranium, i.e., in the frontal bone over the ventricle. This is known in the field as Kocher's point. The burr hole, only slightly larger than the diameter of the selected catheter to ensure a snug fit and provide a seal against CSF leakage, is placed approximately 1 cm. anterior to the coronal suture, approximately 10 to 12 cm. above the nasion, and approximately 2 to 3 cm. from the midline over the nondominant hemisphere. After the burr hole is made, the dura and underlying pia-arachnoid are opened and coagulated, for example, with a fine-tipped blade, after cauterizing the dural surface.

The lateral ventricles of the human brain form an arc parallel to the arc of the cranium, i.e., the contour of the lateral ventricles parallels the arc of the surface of the skull. Thus, a catheter guided perpendicular to the cranial surface at the point of entry into the cranium will enter the ventricular system. Specifically, any line penetrating a burr hole in the surface of the skull at a 90° angle also bisects the lateral ventricle.

Various methods have been utilized in the prior art in an attempt to ensure the correct placement of a catheter device in the patient's cerebral ventrical. One such method involves the use of a pre-measured catheter having a stylet which may be introduced and directed freehand through the burr hole, approximately in the coronal plane, and angled towards the medial canthus of the ipsilateral eye, using external landmarks such as the inner canthus of the eye in the frontal plane and a point just in front of the external auditory meatus in the lateral plane as guided to placement. CSF should flow freely from the catheter tip at a depth of approximately 4 to 5 cm. from the interior cranial surface.

A distinctive "give", or release of opposition, can often be felt when the ventricle is penetrated. Pressure should be measured at this point, however, since an artificially low value will be obtained even if small amounts of fluid are lost. Then, after removal of the stylet from the catheter, advancement another 1 cm. or so should insure placement in the frontal horn at a depth of about 5 to 6 cm. from the external table of the skull, care being taken that CSF continues to flow.

Intraoperative fluoroscopy and air ventriculography, well known techniques in the art, have been used to confirm freehand catheter placement. While these procedures can be helpful in placing the catheter if the ventricles are small, they also add to the complexity of the overall procedure.

Aside from the cost and time constraints of such radiographic confirmation of catheter placement, many published reports of postoperative studies have revealed misplacement of catheter tips in cerebral matter or subarachnoid space. This misplacement results in increased neurological morbidity and the need for additional operation time. Moreover, multiple passes of the catheter into cerebral matter are quite common before the ventricles are properly penetrated. Finally, the anxiety a neurosurgeon experiences when trying to place a catheter by freehand into the ventricular system makes first pass success that much more difficult and further increases the risks involved in the procedure.

A recently developed procedure to ensure correct catheter placement was disclosed and claimed by one of the present applicants in U.S. Pat. No. 4,613,324 (the '324 patent), issued Sep. 23, 1986. The disclosure of that patent is therefore specifically incorporated herein by reference. The apparatus comprises a guide assembly which, when positioned over an orifice drilled in the cranium above the anterior horn of the lateral ventricle, guides a catheter and obdurator through the orifice and into the lateral ventricle at an angle normal to an imaginary plane formed by a tangent to the cranium at the orifice.

The method of utilizing the claimed device of the '324 patent comprises providing an orifice in the cranium just anterior to the coronal suture in a midpupillary line of the cranium and inserting a ventricular catheter containing an obdurator through the orifice towards a lateral ventricle, wherein the catheter containing the obdurator is guided through the orifice, by means of a guide assembly, at an angle normal to an imaginary plane formed by a tangent to the cranium at the orifice.

This orientation of 90° is required for proper placement of the catheter within the ventricular portion of the patient's brain since, if the burr hole deviates by more than about 7 degrees from the perpendicular to a plane tangent to the point on the cranium where the catheter is inserted, the catheter will be directed away from the ventricular region and into other areas of the organ not conducive to the intended purposes of the apparatus disclosed. Thus, aligning the burr hole in such a precise manner greatly simplifies the subsequent task of correctly aligning the catheter within the ventricular cavity.

A recently developed apparatus to ensure drilling an orifice in the human cranium at an angle of substantially 90 degrees to a plane defined by a tangent to the surface of the cranium at the orifice was disclosed and claimed by the present applicants in U.S. Pat. No. 4,821,716 (the "'716 patent"), issued Apr. 18, 1989. The disclosure of that patent is therefore specifically incorporated herein by reference. The apparatus of the '716 patent comprises a drill guide assembly means which, when positioned over the cranium provides a means for guiding a drill used for making an orifice in the cranium.

Another recently developed apparatus for accurately inserting a catheter through an orifice in the human cranium and guiding said catheter into a ventricle of a human brain was disclosed and claimed by the present applicants in U.S. Pat. No. 4,931,056 (the "'056 patent"), issued Jun. 5, 1990. The disclosure of that patent is therefore specifically incorporated herein by reference, as well. The apparatus of the '056 patent comprises a first guide means adapted to rest on the human cranium and a catheter guide means inserted within the first guide means.

The above identified apparatus, have, therefore proven to be a significant improvement over the prior apparatus and methods of the art. However, in using the prior apparatus, visualizing the drill and catheter within the guide assemblies can be intricate and/or difficult. It is therefore desirable to present improved apparatus and methods to further assist in visualizing the drill and the catheter within the guide assemblies. Accordingly, to address this difficulty in the prior art, a rapid, simple, inexpensive and accurate improved apparatus is provided for visualizing the guiding of the drill (for perforation of the patient's cranium at an angle of substantially 90 degrees to the surface) and for visualizing the guiding of the accurate insertion and placement of a ventricular catheter.

SUMMARY OF THE INVENTION

An object of the present invention is to provide an improved method and apparatus for perforating the human cranium, and inserting a catheter therein at an angle of substantially 90 degrees.

It is a further object of the present invention to provide an apparatus for perforating the human cranium which has an opening or a slotted design provided to the catheter guide and drill guide.

It is a further object of the present invention to provide an apparatus and method which provides the neurosurgeon with direct visual access to the drilling point in the cranium.

It is a further object of the present invention to provide an apparatus and method which allows pre-loading of the catheter on the catheter guide.

It is a further object of the present invention to provide an apparatus and method for cranial perforation which allows use of more complex and instrumented catheters by allowing the guides to be removed from the side of the catheter.

It is a further object of the present invention is to provide an improved method and apparatus for perforating and catheterizing a human cranium at an angle of substantially 90 degrees to the surface thereof. This improved method and apparatus facilitates the placement at the required 90 degree angle of a cranial drill and insertion of a catheter through the surface of the cranial bone and into the anterior horn of a lateral ventricle of the patient's brain, by allowing visualization by the neurosurgeon of the cranial drill and catheter during the operative procedure, thus eliminating any difficulties associated with prior art methods and allowing the neurosurgeon to more accurately position the drill and catheter.

It is a further object of the invention is to provide an improved method and apparatus which permits the catheter to be pre-loaded on the catheter guide, allowing the neurosurgeon to place the catheter into the catheter guide and direct it into the ventricular system of the brain without touching the catheter and without compromising sterility.

It is a further object of the invention is to provide an improved method and apparatus which permits a guide to be removed from the side of the catheter rather than over the end of the catheter. This allows for the use of more complex and instrumental catheters that are now available or being developed.

It is a further object of the invention is to provide an improved method and apparatus for guiding a drill through the cranial surface and for guiding the insertion of a catheter into the anterior horn of the lateral ventricle of the human brain which optimizes accurate and reproducible placement of the catheter.

It is a further object of the invention is to provide a method and apparatus for accurately and reproducibly perforating the patient's skull and inserting a catheter through the cranial surface into the anterior horn of a lateral ventricle of the patient's brain in a manner which prevents insertion of the catheter into the cerebral matter or subarachnoid space.

A first embodiment of the present invention comprises an improved apparatus for drilling a hole in a human cranium at an angle of substantially 90 degrees to a surface portion thereof. The improved apparatus comprises a drill guide 10 with drill guide slot or opening 20. The drill guide 10 directs and aligns a drill for cutting through the substrate at a proper angle, i.e., substantially 90 degrees to a plane defined by a tangent to the substrate during the perforation thereof. The drill guide slot or opening 20 allows the neurosurgeon to have direct visual access to the drilling point. This visual access allows the neurosurgeon to more accurately place the drill and also to maintain the drill guide 10 in an accurate position relative to the hole in the cranium for catheter placement. The drill guide slot or opening 20 preferably extends the full height of the member 18. In a preferred embodiment, the drill guide opening is a slot with a width which is between 1 to 3.5 mm to match the width of the catheter guide slot or opening 38.

The improved apparatus further comprises a drill 50, such as that disclosed in U.S. Pat. No. 4,931,056, which is insertable within an open bore portion of the drill guide 10, which is operable to perforate the substrate. As disclosed in the '056 patent, the drill may be provided with a number of spacer rings. The purpose of the spacer rings is to prevent the penetration of drill 50 past a predetermined distance in to the patient's cranium. As drill 50 penetrates the cranium at a certain depth, a lower surface of lower ring contacts the upper portion of tubular member 18 and thus prevents further passage of drill 50 therethrough until at least one ring member is removed. The spacer rings are preferably "C" shaped, but may alternatively be circular or of some other alternative shape. The open portion of the spacer rings engages the shaft 52 of the drill. Any number of desired spacer rings may be employed. In the preferred embodiment, four spacer rings are used.

The improved apparatus further comprises a drill tip where the angle on the tip of the drill bit is designed to prevent skidding. This improved drill tip also makes a very clean hole through the inner table of the cranium. A preferred embodiment of the drill tip is a flattened split point design.

The invention also includes an improved catheter guide 32, having an open bore portion with a diameter reduced in relation to the bore of the drill guide 10, and having a catheter guide slot or opening 38. The catheter guide 32 is insertable within the open bore portion of the drill guide 10 upon removal of the drill therefrom so as to effectively reduce the diameter of the drill guide 10.

The catheter guide slot or opening 38 allows the catheter 100 to be pre-loaded into the catheter guide 32. Thus, the neurosurgeon can place the catheter 100 into the catheter guide 32 and direct it into the ventricular system without touching the catheter and without compromising sterility. The catheter guide slot or opening 38 and drill guide slot or opening 20 allow the drill guide 10 and catheter guide 32 to be removed from the side of the catheter rather than over the end of the catheter 100. These guide slots or openings 38 and 20 allow for the apparatus to be used with more complex and instrumental catheters than would otherwise be possible, including the complex catheters that are currently available or those that are being developed. Other openings to accommodate such complex catheters may be provided consistent with the present invention, as well. Fluid transport means, such as a catheter 100, may be inserted through the catheter guide 32 and thereafter into a ventricular portion of the patient's brain, in order to, for example, drain or shunt CSF therefrom or for the instillation or delivery of pharmacological therapeutic agents.

The drill guide 10 of the embodiment comprises a tubular member 18 with drill guide slot or opening 20 and a support for the tubular member 18. The tubular member 18 is adapted to receive the catheter guide 32. This support is adapted to rest unsecured on the patient's cranium. The support and the tubular member 18 are related to each other and to the cranium so as to guide the catheter through the orifice and in a direction perpendicular to a plane defined by a tangent to the cranium at the orifice, independent of the orientation of the orifice.

The support of the drill guide may comprise a plurality of legs 14, each leg terminating in a free end. The free ends 16 of these legs form a polygon defining a plane and the tubular member 18 guides the catheter through the orifice in a direction perpendicular to this plane defined by the polygon and through the geometric center thereof. In a preferred embodiment, the legs are three in number and of equal length. Therefore, in the preferred embodiment, the polygon is an equilateral triangle formed by the free ends of these legs. In an alternative embodiment, a cone can be used instead of a plurality of legs.

Further, the support may be connected to the tubular member 18 through a connecting platform 12. The platform 12 is preferably contoured to provide indented sections 24. These indented sections make the drill guide 10 more stable by impeding the neurosurgeon from placing his fingers over the platform 12 other than over the sections of the platform 12 which attach to the legs 14. When the neurosurgeon grips the platform 12 over the legs 12 the drill guide 10 is more stable than when the platform 12 is not gripped over the legs 12.

Preferably, the drill guide as described above should be constructed of a rigid, non-deformable material such as thermoplastic or stainless steel.

An insert within the tubular member 18, forming a catheter guide 32, is adapted to be in guiding engagement with the catheter while the free end of the catheter is inserted into the ventricle of the brain. The catheter tubular member 34 is adapted to receive and guide the catheter therethrough. The catheter guide 32 may partially extend into the orifice which has been formed in the cranium. Additionally, this catheter guide 32 has a catheter guide opening 38 which advantageously allows the neurosurgeon to visualize the catheter and direct it without compromising sterility. In the preferred embodiment, the catheter guide opening 30 is a slot which extends the full height of the catheter guide 32. The preferred width of the catheter guide slot 38 is between 1 to 3.5 mm to allow for insertion and removal of a variety of catheter sizes.

Another embodiment of the invention comprises a method for drilling an orifice in a human cranium at an angle at substantially 90° to a plane defined by a tangent to the cranium at the orifice and subsequently inserting a catheter into a ventricular portion of the brain within the cranium. The method initially comprises positioning a drill guide upon a portion of an outer surface of the patient's cranium such that an open tubular portion of the drill guide is oriented at an angle of substantially 90° to a plane defined by a tangent to the cranium at the orifice. The neurosurgeon visualizes the drill point through the drill guide slot or opening 20. This visualization allows the neurosurgeon to achieve accurate 90 degree penetration of the cranium. The drill guide, as described above, comprises a tube with an opening, such as a slot, and a support therefore.

The method further comprises drilling an orifice in the cranium by drilling means proximally anterior to a coronal suture in a midpupillary line of the cranium. The orifice extends through the cranium at an angle of substantially 90° to a plane defined by a tangent to the cranium at the orifice. A catheter guide is thereafter inserted into the open tubular portion of the drill guide so as to render the diameter of the drill guide more consistent with that of a standard catheter.

The catheter may be preloaded on the catheter guide or inserted on the catheter guide when needed. A catheter is subsequently guided through the open portion of the catheter guide and thereafter through the orifice in a direction perpendicular to a plane defined by a tangent to the cranium at the orifice. The opening or slot in the catheter guide allows the neurosurgeon to visualize the catheter during this procedure. Through the use of the present invention, therefore, the catheter accurately penetrates the ventricular portion of the brain upon the first insertion.

In a further embodiment of the invention, the method additionally comprises supporting the drill guide by a support comprising a plurality of legs. The legs are preferably three in number, each terminating in a free end. The free ends thus form a triangle defining a plane. Alternatively, the support can comprise a cone, instead of a plurality of legs.

An alternate embodiment of the invention comprises guiding the catheter through a catheter guide inserted within the drill guide and into the orifice and into the ventricular portion of the patient's brain in a direction perpendicular to the plane defined by the triangle formed by the legs of the support and through the geometric center thereof.

The drilling of the cranium can be performed manually, pneumatically, electrically or hydraulically by use of suitable drilling means. Also, the method includes the step of limiting the depth of penetration of the drilling means to a predetermined distance within the cranium by providing stop means on the drilling means for contacting the drilling guide means.

BRIEF DESCRIPTION OF THE DRAWINGS

The method and apparatus of the present invention will now be described with reference to the accompanying drawing figures, in which.

DETAILED DESCRIPTION OF THE PREFERRED EMBODIMENTS

Figure 1:
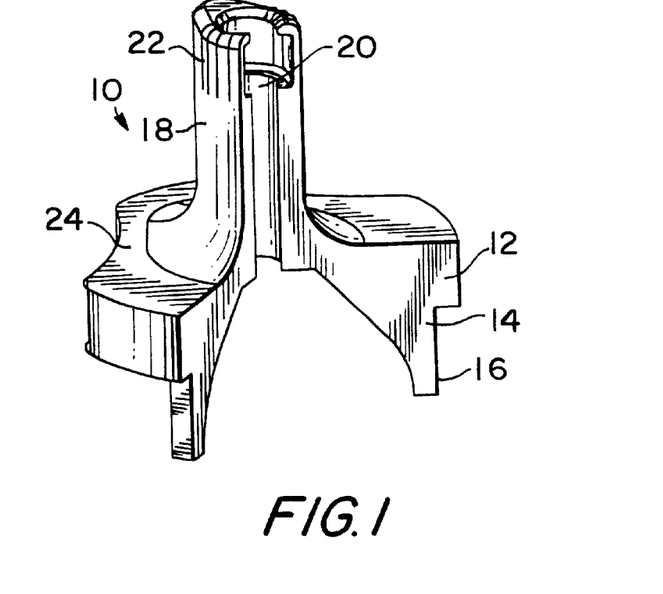
FIG. 1 is a side elevational view of applicants' drill guide.

Turning initially to FIG. 1 there is illustrated drill guide 10 for controlling and directing a twist drill device during the formation of a burr hole through the cranium of a patient. The initial function of drill guide 10 is to control the drill during the perforation of the cranium, thus preventing the bit from skipping on the bone or the scalp, especially at the start of the drilling procedure.

Drill guide 10 may be seated, for example, directly upon the scalp of the patient, above an incision therein measuring on the order of from about 1–2 millimeters. Since, however, the skin of the scalp is loose and prone to movement relative to the cranial bone, the placement of drill guide 10 in one position throughout the operative procedure serves to provide a means for readily locating the burr hole located beneath the incision. Since the diameter of the catheter placed within the burr hole ranges between only about 2–3 millimeters, the hole in the cranium need not be much greater in size, if at all, and it may therefore be difficult to relocate without the assistance of drill guide 10.

Alternately, in the event a larger incision is made and drill guide 10 is seated directly upon the surface of the skull, its legs spread apart the surrounding scalp tissue and prevent such tissue from being gathered or drawn to the drill bit during the operation, thus protecting the scalp from injury. Drill guide 10 is thus preferably constructed of a rigid, non-deformable material such as a rigid engineering plastic or a metal such as stainless steel in order to fulfill these functions. The entire apparatus may be manufactured inexpensively from a plastic material, as a disposable assembly, thus reducing the cost of the assembly and assuring a sharp, sterilized drilling device for each operation. The availability of such a pre-sharpened, sterilized drilling device also serves to reduce the time required to complete each operation.

As shown in FIG. 1, drill guide 10 further comprises platform 12. Extending from platform 12 in a diverging manner are three legs 14, which terminate in free ends 16. Free ends 16 of legs 14 define a triangle lying within a defined plane. Drill guide 10 further includes guide means for guiding the drill in a direction perpendicular to the plane defined by the triangle formed by legs 14 and through the geometric center thereof. The guide means comprises a tubular member 18 extending through platform 12 in a direction perpendicular to the triangular plane described above.

Tubular member 18 is hollow, defining a central lumen to permit the passage therethrough of a drilling device (described in the U.S. Pat. No. 4,931,056). The diameter of this lumen is not critical but it must, at a minimum, be sufficient to permit the passage of the drill. In accordance with the invention, tubular member 18 is further provided with a drill guide slot or opening 20. The drill guide slot or opening 20 allows the neurosurgeon to have direct visual access to the drilling point. This visual access allows the neurosurgeon to more accurately place the drill and also to maintain the drill guide 10 in an accurate position relative to the hole in the cranium for catheter placement. When drill guide 10 is placed on the patient's cranium with the free ends 16 of legs 14 resting thereupon, the plane of the triangle defined by free ends 16 coincides with or is parallel to a plane tangent to the cranial surface directly below tubular member 18.

Accordingly, drill guide 10 directs the drilling device perpendicular to this tangential plane, ensuring the production of a burr hole through the cranial bone at an angle of 90 degrees to the surface of a plane tangent to the cranium. This alignment assures that a ventricular catheter, inserted into the brain in a direction perpendicular to the curvature of the cranium, will not deviate from a preferred course due to a misaligned skull hole. As noted above, if the orientation of the bore hole deviates by more than about 7 degrees from the perpendicular to a plane tangent to the cranium at the point of insertion of the catheter, the catheter is much more likely to be misaligned and to miss the ventricular portions of the brain entirely.

Preferably, legs 14 of drill guide 10 are of equal length, equidistantly spaced and symmetrically disposed relative to each other, whereby the free ends 16 define an equilateral triangle. Tubular member 18 directs the drill perpendicular to the plane defined by this equilateral triangle at the geometric center thereof and hence, perpendicular to the tangent plane upon the surface of the patient's cranium.

It is however, nevertheless possible to practice the invention with a drill guide 10 having an asymmetric arrangement of legs 14, as long as the guide means, i.e., tubular member 18 of drill guide 10, extends perpendicularly to the plane defined by the free ends 16 of legs 14 and the drill guide 10 is placed on the cranial surface such that this plane coincides with or is parallel to a plane tangent to the cranium at the orifice.

Similarly, the invention may be practiced with a drill guide 10 having more than three legs, as long as the above-described directional criteria are maintained. For example, a cone shaped support can be used instead of legs. Additionally, while tubular member 18 is illustrated as being cylindrical in shape, any shape which allows an unencumbered passage of the drill there-through may be employed.

While the preferred embodiment of drill guide 10, as described above, includes platform 12 for connecting legs 14 to tubular member 18, platform 12 is not an essential element of drill guide 10. Thus legs 14 may be connected directly to tubular member 18 as long as tubular member 18 guides the drill in the direction perpendicular to the plane of the triangle formed by the free ends 16 of legs 14 and through the geometric center of the triangle.

The height of drill guide 10 and the distance between free ends 16 of legs 14 may be varied, as long as the following principles are observed. First, the base portion of drill guide 10 must preferably form an equilateral triangle defined by free legs 16 of legs 14. Secondly, a line passing through the central lumen of tubular member 18 must be normal to the plane of the triangle thus defined and must pass through the geometric center thereof. Furthermore, the internal diameter of the central lumen may be varied, as long as the lumen is constructed of a sufficient width to accept applicants' twist drill.

Preferably, the distance between free ends 16 of legs 14 ranges from about 1 cm to about 6 cm. The lower limit is established based on the smallest burr hole or orifice necessary for passing a catheter therethrough. These catheters may range from about 2–3 millimeters in diameter. The upper limit is established based on the change in skull curvature which occurs when the midline of the skull is crossed.

Specifically, since the orifice or burr hole is drilled generally from about 2 cm to about 3 cm from the midline, an upper limit of about 6 cm is preferred so that one or more legs do not rest on the skull at a point beyond the midline where the skull curvature has changed. This would place drill guide 10 at such an angle that tubular member 18 would not be directed normal to the imaginary plane defined by a tangent to the orifice at the point of entry.

The specific height of drill guide 10 is also not a critical parameter. A preferred height range is about 2 cm to 10 cm. The lower limit is established on the basis of the usual length of a catheter (15 cm) minus the standard intracranial distance to the ventricle (5 cm).

Although the drill guide 10 of the present invention has been illustrated with three legs 14, this is not a critical limitation. For example, drill guide 10 of the present invention may be constructed with four legs. In such an embodiment, the free ends of each of the four legs define the corners of a polygon such as a square or rectangle and the axis of tubular member 18 passes through the geometric center of the square or rectangle, wherein the axis is normal to the plane thereof. In yet a further embodiment, a cone shaped support can be used, as long as the support meets the geometric criteria described herein.

Figure 9:
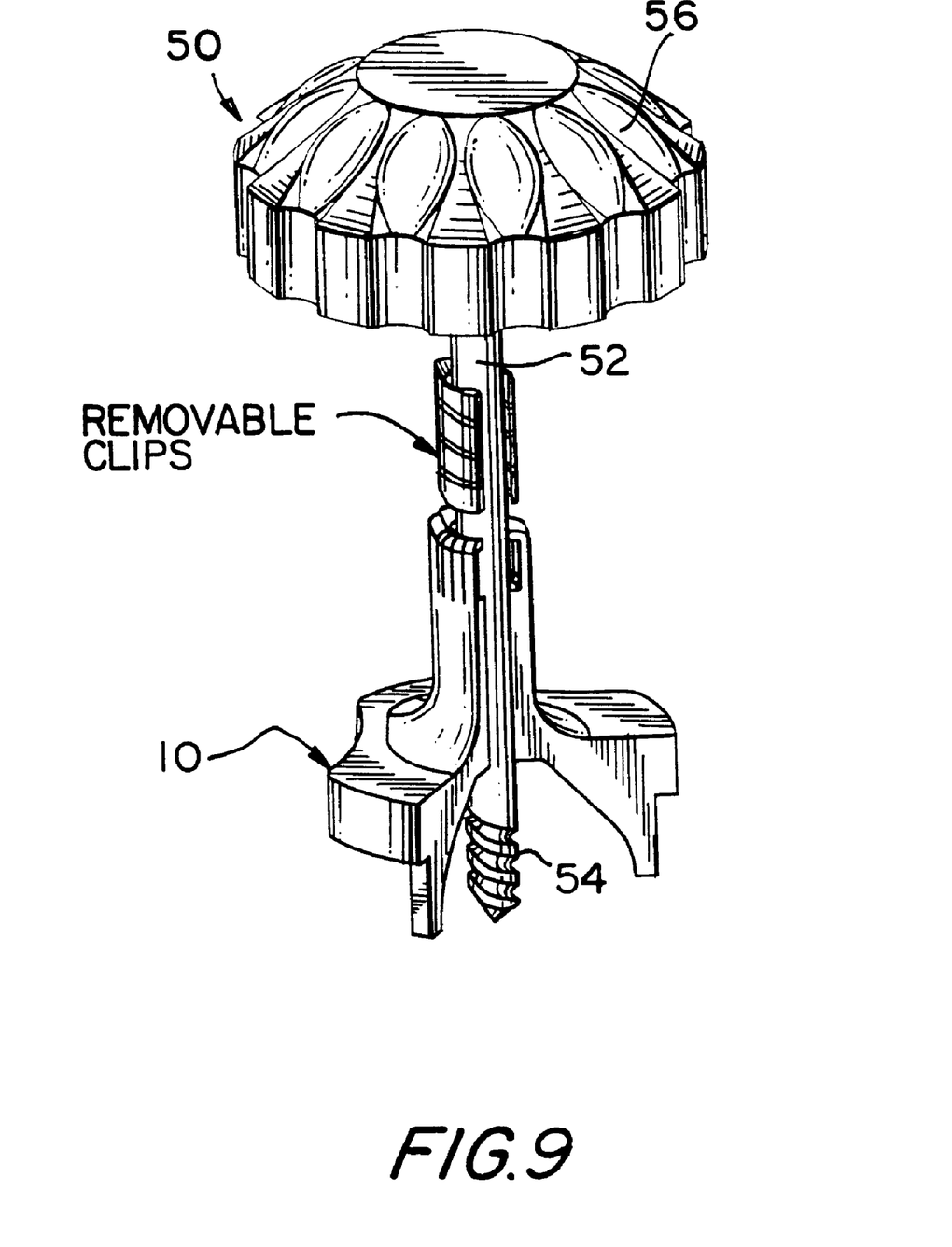
FIG. 9 is a perspective view of applicants' guide assembly with drill, and with removable clips for limiting the depth of penetration of the drill.
Figure 10A:
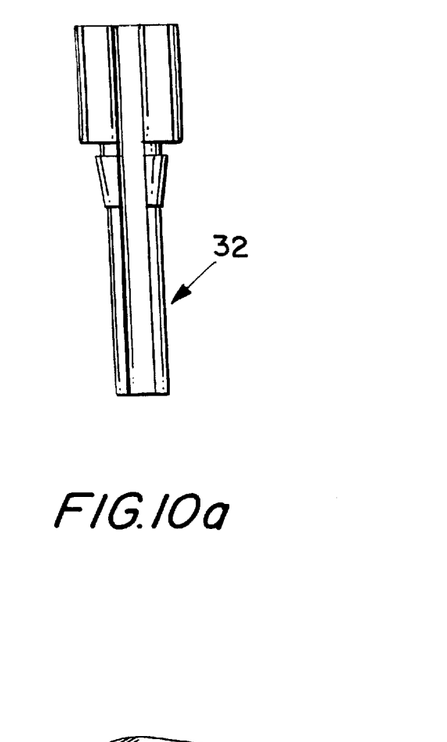
FIG. 10A is a plan view of applicants' catheter guide.
Figure 10B:
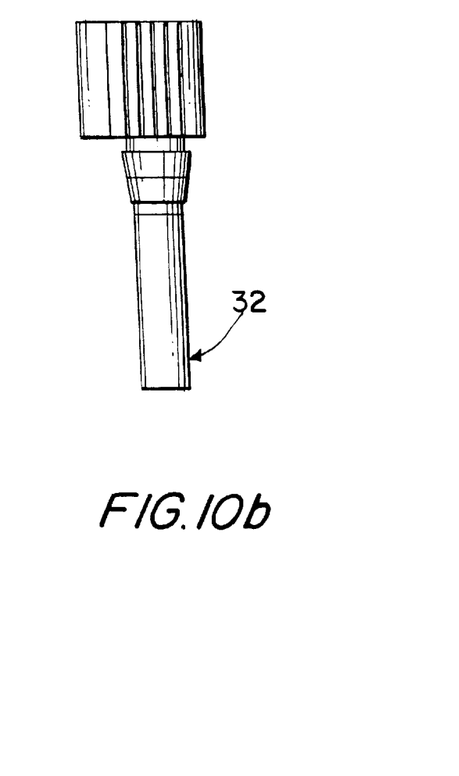
FIG. 10B is a side plan view of applicants' catheter guide.
Figure 10C:
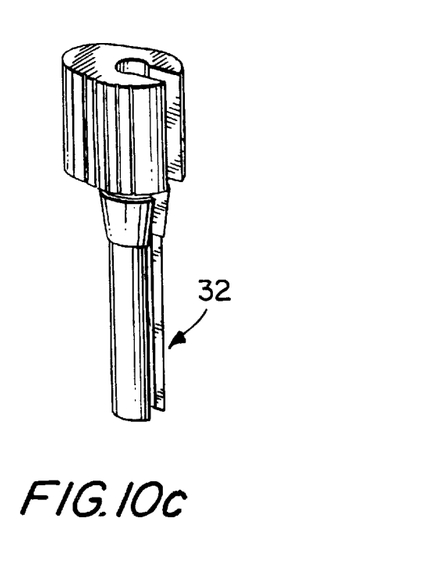
FIG. 10C is a perspective view of applicants' catheter guide.
Figure 10D:
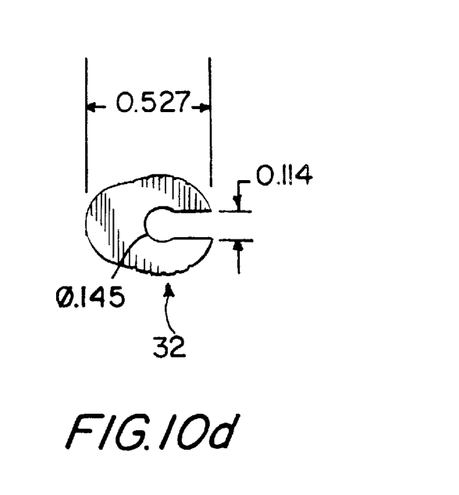
FIG. 10D is a cross sectional view of applicants' catheter guide.

In the event, therefore, that a patient is to undergo a ventriculostomy procedure, drill guide 10 is seated upon the patient's scalp over a small incision made therein or, alternately, directly over the skull itself. Shaft 52 of drill 50 is then inserted into the tubular member 18 of drill guide 10 to a point where drill bit 54 contacts the patient's cranium. A perforation is subsequently made through the cranial bone by the surgeon pressing on and turning the handle of drill 56 with one hand while holding drill guide 10 with the other hand.

As noted above, in the event that drill guide 10 is removed from the surface of the cranium prior to the completion of the procedure, it would be difficult if not impossible to relocate the site to the burr hole under the small, i.e., 1 cm, incision customarily made in the scalp for this purpose. The device thus produces a burr hole at an angle of substantially 90 degrees to a plane defined by a tangent to the surface of the cranium, thus assuring that a catheter width is subsequently to be inserted into the ventricular portion of the brain, perpendicular to the curvature of the cranium, will not deviate due to a misaligned skull hole.

Figure 3:
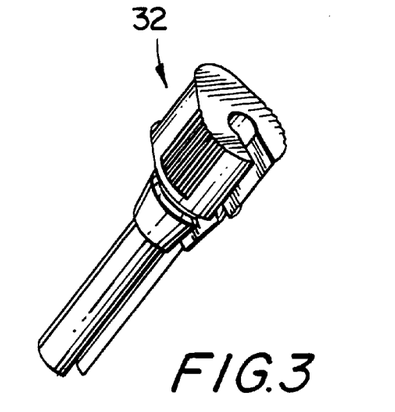
FIG. 3 is a perspective view of applicants' catheter guide.
Figure 4:
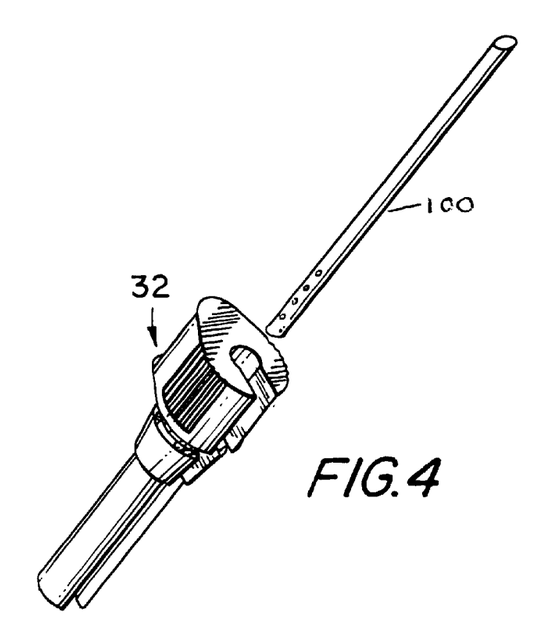
FIG. 4 is an exploded perspective view of applicants' catheter guide with catheter.
Figure 5:
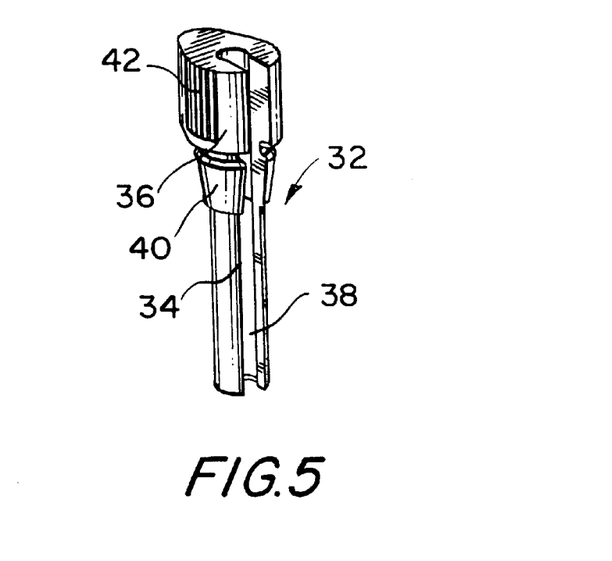
FIG. 5 is a side elevational view of applicants' catheter guide, configured for insertion into the drill guide of the invention.
Figure 6:
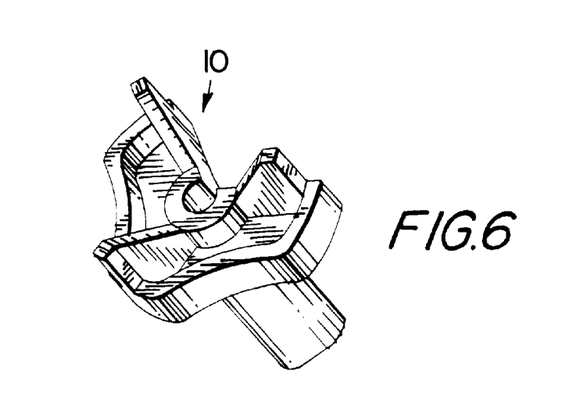
FIG. 6 is a perspective view of applicants' drill guide.
Figure 7:
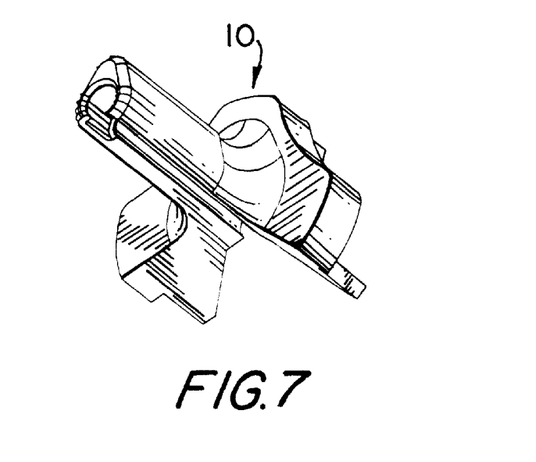
FIG. 7 is another perspective view of applicants' drill guide.
Figure 8:
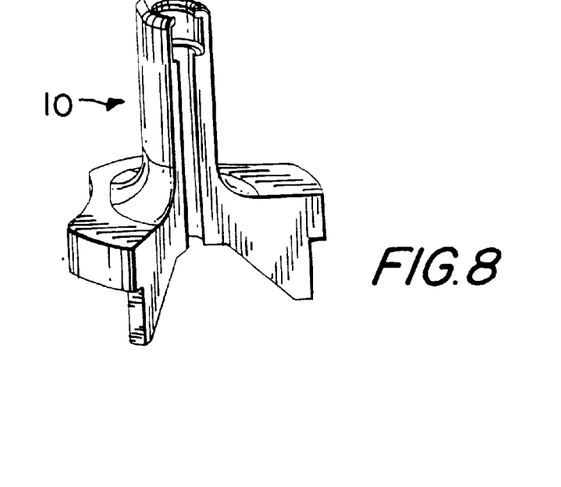
FIG. 8 is still another perspective view of applicants' drill guide.

Once the bore hole has been prepared at an angle of substantially 90 degrees to a plane tangent to the surface of the patient's cranium, drill 50 is removed from the drill guide 10 and catheter guide 32 is inserted into catheter tubular member 34 with a lumen having reduced diameter relative to tubular member 18 of drill guide 10. Catheter guide 32 is further provided with a relatively wider top portion 36 which can be used to position catheter guide 32 within drill guide 10. Catheter tubular member 34 of catheter guide 32 has a catheter guide slot or opening 38. The catheter guide slot or opening 38 allows the catheter 100 to be pre-loaded into the catheter guide 32. Thus, the neurosurgeon can place the catheter 100 into the catheter guide 32 and direct it into the ventricular system without touching the catheter and without compromising sterility.

The catheter guide slot or opening 38 and drill guide slot or opening 20 allow the drill guide 10 and catheter guide 32 to be removed from the side of the catheter rather than over the end of the catheter. This allows the more complex and instrumental catheters that are now available or are being developed to be used with the present devices. These complex catheters can be inserted and removed from the catheter guide slot or opening and the drill guide slot or opening with ease, as opposed to the catheter guides and drill guides of the prior art which do not accept such complex catheter devices. In accordance with the present invention, the catheter guide slot or opening 38 and the drill guide slot or opening 20 each accommodate projections off of the catheter, including tubing, instrumentation or any other protuberances or additions to the catheter which are desired or to be developed in the art.

Although the disclosed slot is the preferred opening in the disclosed devices for allowing protuberances off of the catheter, it is understood that other openings, whether of different size or shape, or even multiple openings, can be provided to the catheter guide and/or the drill guide consistent with the present invention. In general, it is provided that the devices be provided with an opening or design suited to accommodate projections or protuberances off of a catheter, or additions to a catheter, to allow the present devices to be used with more complex and developed catheters that consist of more than merely a straight length of tubing.

Figure 11A:
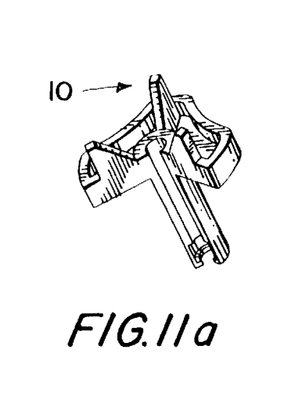
FIG. 11A is a perspective view of applicant's drill guide.
Figure 11B:
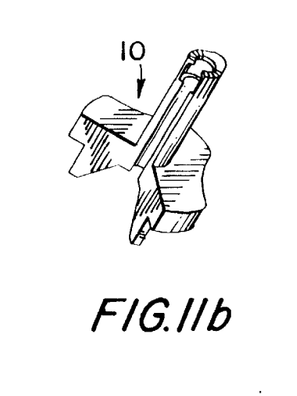
FIG. 11B is another perspective view of applicant's drill guide.
Figure 11C:
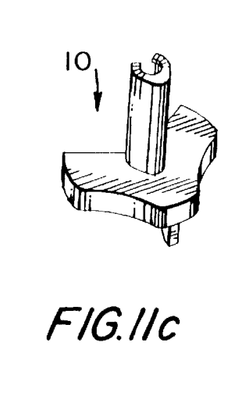
FIG. 11C is another perspective view of applicant's drill guide.
Figure 11D:
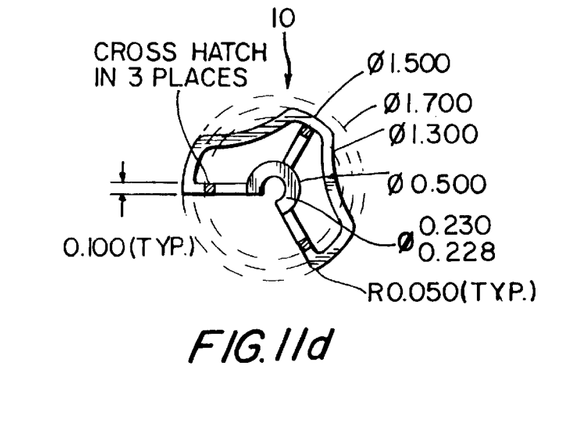
FIG. 11D is a cross-sectional view of applicant's drill guide.
Figure 11E:
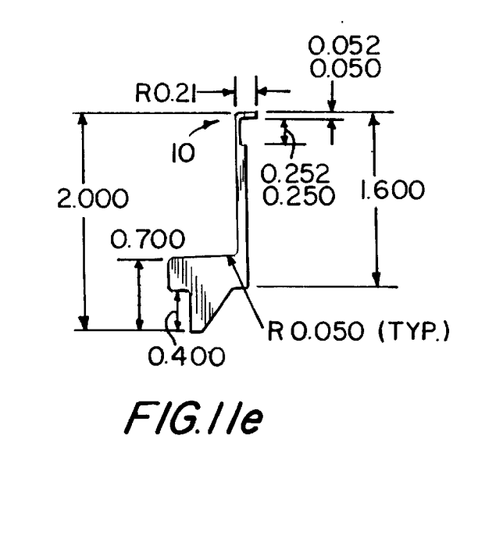
FIG. 11E is a diagram showing measurements of applicant's drill guide.
Figure 11F:
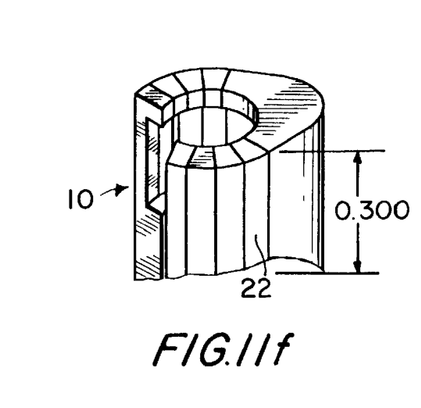
FIG. 11F is a partial perspective view of the top of applicant's drill guide.
Figure 11G:
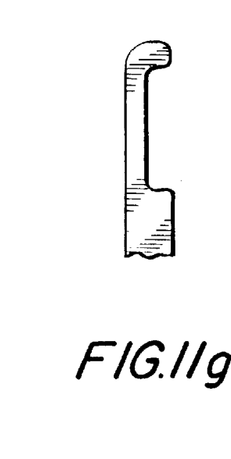
FIG. 11G is a diagram showing measurements of applicant's drill guide.
Figure 11H:
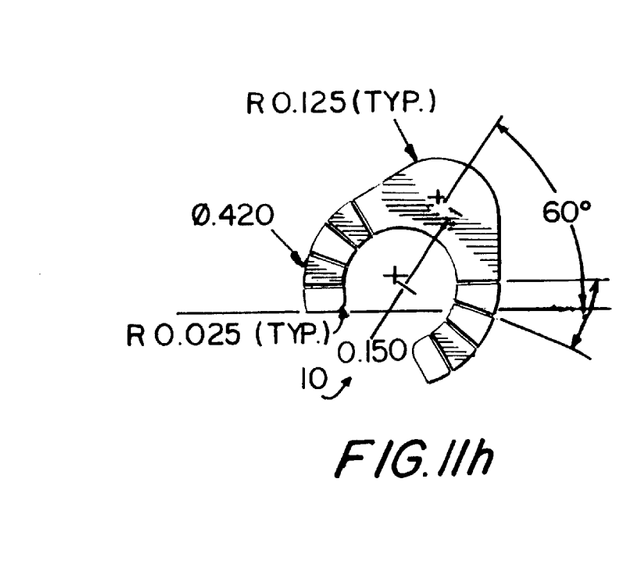
FIG. 11H is a diagram of the top of applicant's drill guide.
Figure 11I:
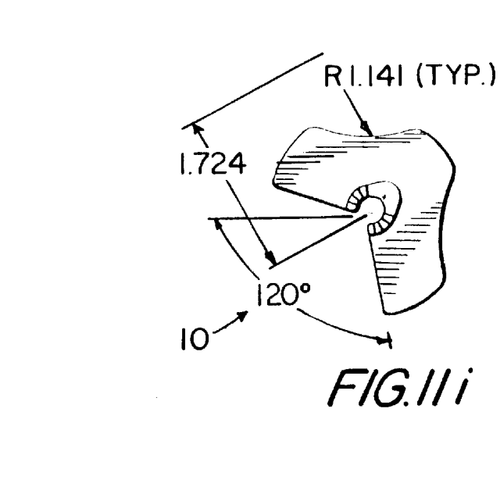
FIG. 11I is a diagram showing the top of applicant's drill guide.

The drill guide 10 has a locking receiver 22 which comprises striations molded into the top of the drill guide 10. The locking receiver 22 is at the top portion of the tubular member 18 and mates with the locking tabs 40 of catheter guide 32. The locking tabs 40 of catheter guide 32 are attached between the top 36 and catheter tubular member 34. The locking tabs 40 insert into the tubular member 18 of the drill guide and lock with the locking receiver 22 to prevent displacement of the catheter guide 32 relative to the drill guide 10. The top 36 in a preferred embodiment has ribs 42 which allows the neurosurgeon to have a good finger grip.

Drill 50 operates within drill guide 10 and is visible to the neurosurgeon through drill guide slot or opening 20. As noted above, drill 50 is inserted into tubular member 18 of drill guide 10 until the point of drill bit 54 contacts the cranium. Handle 56 is then grasped by the surgeon and rotated until the drill bit 54 passes completely through the cranium. Thereafter, the underlying dura and pia-arachnoid tissue may be pierced with the assistance of a needle inserted therethrough and thus prepared for the passage of a catheter.

Once the formation of burr hole is completed, catheter guide 32 is inserted within the tubular member 18 of drill guide 10, as shown in FIG. 1. As noted previously, the purpose of catheter guide 32 is to reduce the lumen diameter of drill guide 10 to a size more correlative with that of catheter 100 to be inserted therethrough.

In an alternative, preferred embodiment of the invention, catheter guide 32 may be constructed having a length sufficient to pass completely through drill guide 10 and at least partially into the burr hole. In the event, therefore, that the guide assembly is moved or is removed from the patient's cranium for any reason, the burr hole may be easily relocated by positioning drill guide 10 over the incision in the patient's scalp and simply rotating the assembly until catheter guide 32 slips into the burr hole for the convenient passage of catheter 100 therethrough into the ventricular portion of the brain.

A burr hole may be drilled on the right or left side of a patient's cranium in the midpupillary line. The orifice is located above the anterior horn of lateral ventricle approximately 10 cm. posterior to the nasion and approximately 3 cm. lateral to midline 46 of the cranium. After drilling of the orifice is complete, the dura and underlying a pia-arachnoid (not shown) are cut and coagulated, in a manner well known in the art.

Figure 2:
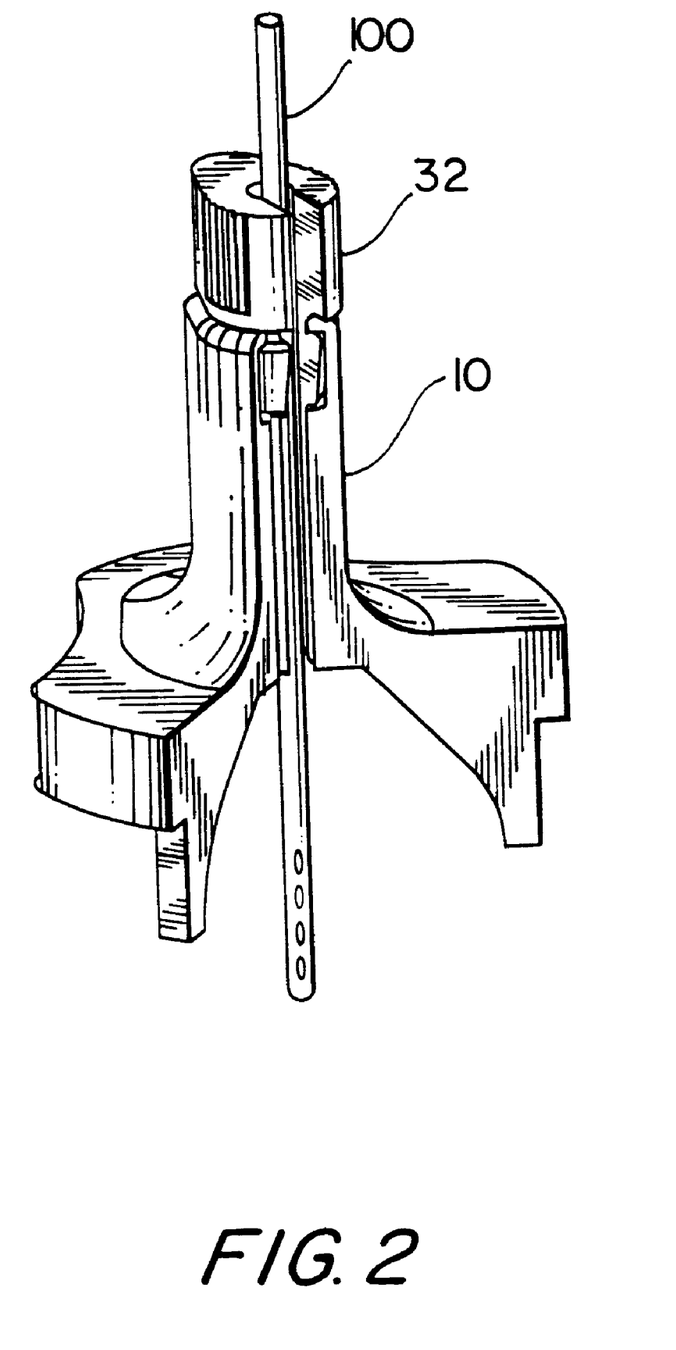
FIG. 2 is a perspective view of applicants' guide assembly with catheter.

A catheter 100 containing a rigid obturator (not shown) is then accurately guided through the orifice and dural opening into the ventricle by the drill guide 10 and catheter guide 32 assembly, which is placed and rests on the skull over the orifice. Any well known catheter 100 and obturator, such as the commercially-available Codman Accu-flo ventricular catheter and obturator, made by the Codman and Shurtleff, Inc., may be used in the present invention.

Accordingly, drill guide 10 and catheter guide 32 assembly will direct catheter 100 perpendicular to the tangent plane described above at the center of the burr hole, ensuring the correct positioning of catheter 100 within the ventricular system of the patient's brain. Subsequent to such entry, the obturator is withdrawn, leaving catheter 100 in place to perform its intended function.

The method and apparatus of the present invention thus insures optimal ventricular catheter placement. The invention may thus be used in any situation requiring placement of a catheter in the ventricular system, e.g., intracranial pressure monitoring, drainage or shunting of cerebral-spinal fluid and the introduction of pharmacologic therapeutic agents. Moreover, the present invention is so anatomically consistent that it can be employed as a reference point for biopsy brain lesions.

The present invention thus eliminates the complications often encountered due to the anxiety ordinarily experienced by neurosurgeons regarding the insertion of a catheter. Patient care is thus improved by eliminating these complications and the associated morbidity. A reduction in the cost to the patient is also achieved by eliminating the need for intraoperative radiographic monitoring and by decreasing operating room time.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A catheter guide and drill guide apparatus for allowing visualization and access to a catheter, comprising, a drill guide and a catheter guide, said drill guide comprising a tubular member defining a central lumen to permit the passage there through of a drill and to allow for the insertion therein of said catheter guide, said tubular member having a drill guide slot; and said catheter guide, comprising a catheter tubular member defining a catheter guide opening to permit the passage there through of said catheter, said catheter tubular member having a catheter guide slot, whereby the catheter guide slot is alignable with the drill guide slot, thereby allowing the operator to visualize and have access to the catheter when said catheter is inserted in said catheter guide and when the catheter guide slot is aligned with the drill guide slot, and allowing for the removal there through of the catheter.

2. A catheter guide and drill guide apparatus, as claimed in claim 1, wherein said drill guide further comprises a platform having a plurality of legs, wherein said platform is connected to said tubular member of said drill guide such that said legs are not located within an access way to said drill guide slot, thereby allowing visualization and access there through.

3. A catheter guide and drill guide apparatus, as claimed in claim 2, wherein said platform is contoured to provide a plurality of indented sections, to facilitate holding the drill guide without impeding visualization through said drill guide slot.

4. A catheter guide and drill guide apparatus, as claimed in claim 2, wherein said tubular member has a locking receiver which comprises striations molded into the top of said tubular member; and said catheter guide has a plurality of locking tabs, whereby said locking receiver mates with said plurality of locking tabs of said catheter guide to prevent displacement of said catheter guide relative to said drill guide.

5. A catheter guide and drill guide apparatus, as claimed in claim 2 wherein said catheter guide has a top having a plurality of ribs which allow the operator to have a good finger grip on said catheter guide.

6. A catheter guide and drill guide apparatus, as claimed in claim 1, wherein said tubular member of said drill guide has a locking receiver which comprises striations molded into the top of said tubular member; and said catheter guide has a plurality of locking tabs, whereby said locking receiver mates with said plurality of locking tabs of said catheter guide to prevent displacement of said catheter guide relative to said drill guide.

7. A catheter guide and drill guide apparatus, as claimed in claim 1, wherein said catheter guide has a top having a plurality of ribs which allow the operator to have a good finger grip on said catheter guide.

* * * * *